(12) United States Patent
Iglesias

(10) Patent No.: US 8,805,472 B2
(45) Date of Patent: Aug. 12, 2014

(54) TREATMENT OF FEMALE STRESS URINARY INCONTINENCE

(75) Inventor: Ramon Jose Iglesias, DeLeon Springs, FL (US)

(73) Assignee: Remendium Labs LLC, Baton Rouge, LA (US)

( * ) Notice: Subject to any disclaimer, the term of this patent is extended or adjusted under 35 U.S.C. 154(b) by 115 days.

(21) Appl. No.: 13/503,235

(22) PCT Filed: Oct. 22, 2010

(86) PCT No.: PCT/US2010/053712
§ 371 (c)(1),
(2), (4) Date: Jul. 6, 2012

(87) PCT Pub. No.: WO2011/050252
PCT Pub. Date: Apr. 28, 2011

(65) Prior Publication Data
US 2012/0265049 A1   Oct. 18, 2012

Related U.S. Application Data

(60) Provisional application No. 61/253,996, filed on Oct. 22, 2009.

(51) Int. Cl.
*A61B 5/05* (2006.01)
*A61B 8/14* (2006.01)

(52) U.S. Cl.
USPC ............................ 600/409; 600/424; 600/466

(58) Field of Classification Search
USPC ............ 600/407, 409, 554, 587, 591; 606/11, 606/14, 15; 607/138
See application file for complete search history.

(56) References Cited

U.S. PATENT DOCUMENTS

| 5,328,077 | A | 7/1994 | Lou |
| 6,086,549 | A | 7/2000 | Neese et al. |
| 6,679,854 | B2 | 1/2004 | Honda et al. |
| 7,837,682 | B2 * | 11/2010 | Ostrovsky et al. ............... 606/41 |
| 2003/0028180 | A1 | 2/2003 | Franco |
| 2006/0074289 | A1 | 4/2006 | Adler et al. |
| 2009/0306509 | A1 * | 12/2009 | Pedersen et al. ............... 600/446 |

FOREIGN PATENT DOCUMENTS

| WO | 96/05768 A1 | 2/1996 |
| WO | 2006/107930 A2 | 10/2006 |

OTHER PUBLICATIONS

International Search Report as issued in connection with PCT/US2010/053712, dated Dec. 27, 210.

* cited by examiner

*Primary Examiner* — Michael Rozanski
(74) *Attorney, Agent, or Firm* — Wiley Rein LLP

(57) ABSTRACT

The present invention relates to the diagnosis and treatment of stress urinary incontinence. In one embodiment, the diagnosis and treatment involves the use of a positional feedback catheter. Positional sensors may be embedded in the catheter to provide real-time tracking of the position and movement of the catheter.

12 Claims, 2 Drawing Sheets

TREATMENT OF FEMALE STRESS URINARY INCONTINENCE

CROSS-REFERENCE TO RELATED APPLICATIONS

The present application is related to and claims the benefit under 35 U.S.C. §119(e) of U.S. provisional patent application Ser. No. 61/253,996, filed Oct. 22, 2009, which is expressly incorporated fully herein by reference.

BACKGROUND OF THE INVENTION

The present invention relates to the diagnosis and treatment of stress urinary incontinence. In one embodiment, the diagnosis and treatment involves the use of a positional feedback catheter. Positional sensors may be embedded in the catheter to provide real-time tracking of the position and movement of the catheter.

Stress urinary incontinence (SUI), also known as effort incontinence, is due essentially to the insufficient strength of the pelvic floor muscles, which leads to the most common etiology of SUI, namely hypermobility of the bladder neck. SUI may present the loss of small amounts of urine associated with coughing, laughing, sneezing, exercising or other movements that increase intra-abdominal pressure and thus increase pressure on the bladder. The urethra is supported by fascia of the pelvic floor. If this support is insufficient, the urethra can move downward at times of increased abdominal pressure, allowing urine to pass.

In women, physical changes resulting from pregnancy, childbirth, and menopause often contribute to stress incontinence. Stress incontinence can worsen during the week before the menstrual period. At that time, lowered estrogen levels may lead to lower muscular pressure around the urethra, increasing chances of leakage. The incidence of stress incontinence increases following menopause, similarly because of lowered estrogen levels. In female high-level athletes, effort incontinence occurs in all sports involving abrupt repeated increases in intra-abdominal pressure that may exceed perineal floor resistance.

It is thought that the principal cause of stress urinary incontinence (SUI) is pregnancy and childbirth and the consequent tearing of the tissues that support the bladder and urethra.

In an attempt to correct this defect, various surgeries have been devised, all with the intent of repositioning the bladder and urethra to their proper place by either a vaginal or abdominal surgical approach. These surgical connections would be highly successful if the bladder and bladder neck could be restored to their natural position. Unfortunately, current surgeries have the high failure rate of approximately 60% due to the lack of a definitive way of checking whether the positioning is correct during any of the surgeries.

Currently, the surgeon pulls the bladder neck into an approximate position, usually through the vaginal wall. The position is approximate because the surgeon cannot actually see, and thus must assume, through experience, the correct position.

This guess is later confirmed correct or incorrect through the passage of time and or the willingness of the patient to complain about the SUI or the recurrence of the SUI, in which case, the patient would be subjected to yet another possibly unsuccessful surgery.

Each time a surgery is performed there is an increased amount of scar tissue. The general immobilization of the tissues will increase after subsequent surgeries, which will adversely affect the subsequent success/failure rate of these surgeries. There is a genuine need for the surgeon to be able to watch the bladder and its position in real time as the surgery progresses in order to avoid more surgeries and to correct the SUI during the initial procedure.

By watching the positioning in real time, the surgeon would be able to position the bladder neck and the urethra correctly and not have to guess at the proper placement. It would no longer be a blind procedure leaving the bladder too tight or at times too loose or subject to the happenstance of a correct positioning.

One of the most accurate tools currently available for diagnosing urinary incontinence is a cystourethrogram. The diagnoses of urinary incontinence using this method are based on difficult to interpret pressure variants, which may lead to misdiagnoses of SUI versus urge incontinence versus neurological defect. Often, presently available diagnostic methods test the patient in the dorso lithotomy position during which time stress urinary incontinence does not occur. Rather, a patient should be tested instead under the same event that causes incontinence, such as coughing, running, jumping, etc., making the diagnosis of the etiology more accurate by monitoring the mobilization of the patient's pelvic floor during the event that causes the incontinence.

BRIEF SUMMARY OF THE INVENTION

The present invention relates to a device comprising at least one sensor capable of providing positional feedback. In one embodiment, the device may be a catheter. In another embodiment, the device may be a Foley catheter.

The sensor capable of providing positional feedback may transmit, receive and/or store magnetic, electromagnetic, microelectromechanical, radio frequency, ultrasound or video data. In one embodiment, the sensor may be an accelerometer. In another embodiment, the sensor may be a gyroscope. In yet another embodiment, more than one sensor of differing types may be located within or on the device.

The present invention further relates to a method for sensing the position of the bladder relative to a fixed reference point within the body by inserting a positional sensor enabled catheter within the bladder. The fixed reference point within the body may be the pubic bone, the coccyx or the vagina. The method may be performed in real-time, for example, during an operation. In another embodiment, the method may be performed at multiple time intervals. The multiple time intervals may occur, for example, pre- and post-event, wherein the event may be pregnancy or menopause.

In another embodiment of the present invention, a method is provided for treating female stress incontinence wherein a positional sensor enabled catheter may be inserted into the bladder; the position of the bladder may be determined relative to a fixed reference point within the body; and then, the bladder may be manipulated to a position suitable for alleviating the incontinence. In an embodiment, the bladder position may be determined relative to the pubic bone, the coccyx or the vagina. In a further embodiment, the method may be performed during a real-time operation.

BRIEF DESCRIPTION OF THE DRAWINGS

FIG. 1b is a cross-section of the catheter of FIG. 1a.

DETAILED DESCRIPTION OF THE INVENTION

Figure 1A:
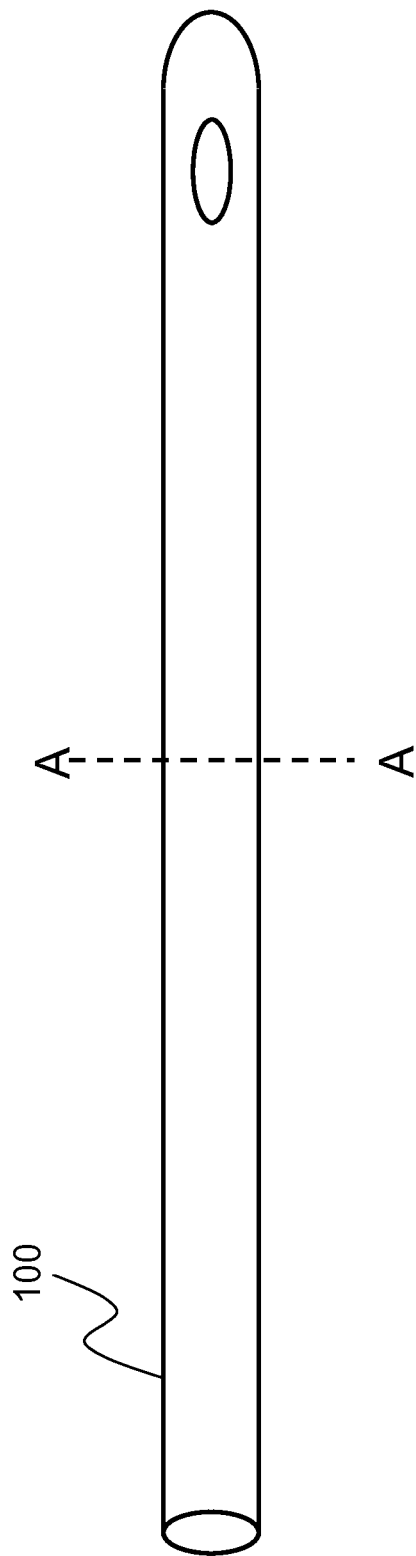
FIG. 1a depicts a lateral view of an embodiment of the present invention.

When used in the claims, the terms "a" and "an" and "the" and similar references in the context of describing the invention (especially in the context of the following claims) are to be construed to cover both the singular and the plural, unless otherwise indicated herein or clearly contradicted by context. Also when used in the claims, the terms "comprising," "having," "including," and "containing" are to be construed as open-ended terms (i.e., meaning "including, but not limited to,") unless otherwise noted. To the extent used, the recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Variations of the embodiments may become apparent to those of ordinary skill in the art upon reading the description. Accordingly, this invention includes all modifications and equivalents of the subject matter recited in the claims appended hereto as permitted by applicable law. Moreover, any combination of the described elements in all possible variations thereof is encompassed by the invention unless otherwise indicated herein or otherwise clearly contradicted by context.

For purposes of the present invention, the term "urethra" may be defined as the canal leading from the bladder, discharging the urine externally. See STEDMAN'S MEDICAL DICTIONARY, at page 2072 ($28^{th}$ ed.). In females, the urethra is a canal about 4 centimeters long passing from the bladder, in close relation with the anterior wall of the vagina and having a long axis that parallels that of the vagina opening in the vestibule of the vagina posterior to the clitoris and anterior to the vaginal orifice. Id. The term "urinary bladder" refers to a musculomembranous elastic bag serving as a storage place for the urine, filled via the ureters and drained via the urethra. Id. at page 226. The term "bladder neck" is defined as the smooth muscle of the bladder neck is histologically, histochemically and pharmacologically distinct from the detrusor muscle proper and so the bladder neck should be considered as a separate functional unit. See GRAY'S ANATOMY, at page 1290 ($39^{th}$ ed.). The arrangement of smooth muscle in this region is quite different in males and females, and therefore each sex is described separately. In females, the bladder neck consists of morphologically distinct smooth muscle. The large diameter fasciculi characteristic of the detrusor are replaced in the region of the bladder neck by small diameter fasciculi which extend obliquely or longitudinally into the urethral wall. Id. In the normal female the bladder neck which above the pelvic floor supported predominantly by the pubovesical ligaments, the endopelvic fascia of the pelvic floor and levator ani. These support the urethra at rest; with elevated intra-abdominal pressure the levators contract increasing urethral closure pressure to maintain continence. This anatomical arrangement commonly alters after parturition and with increasing age, such that the bladder neck lies beneath the pelvic floor, particularly when the intra-abdominal pressure rises. The mechanism described above may fail to maintain continence (stress incontinence as a result of urethral hypermobility).

In the present invention, for example, a Foley catheter could be lined with sensors that transmit a signal sending their position to a computer screen. Below the firm tip of the Foley catheter, e.g., about ½ inch, a small section of the device would be filled with normal saline solution in order to find the neck of the bladder.

By operating with an image of where the bladder and urethra are in the patient relative to the pubic bone, the coccyx or the vagina in real time during the procedure, the surgeon would be able to pull the bladder and the urethra to a position considered normal under direct observation and not merely by guessing how tight or how loose to position the anatomy.

The positional sensor enabled Foley catheter would be invaluable as a study/diagnostic tool for the surgeon as well as the patient who is considering a pregnancy. The practitioner may be able to provide the patient with an in-office procedure that would determine a baseline position and a relative mobilization of the bladder (baseline) before the possible damage to her pelvic floor that may occur during pregnancy and delivery, so when the surgical repair, if needed, is performed, her bladder can be re-positioned to the original anatomic position. Surgery would only be performed on patients with a surgically correctable structural defect.

The positional sensor enabled Foley catheter would also help with any diagnosis where surgery is an option and the position of the bladder needs to be adjusted surgically to correct any urinary problem, such as that involving a woman who cannot empty her bladder due to avulsion of the bladder through the vagina. In males, prostactic hypertrophy causes a stricture of the urethra. The diagnosis of urethral stricture is usually made by the patient's history and confirmed after an operative cystogram. The diagnosis of urethral stricture could be made by using a positional sensor enabled Foley catheter much like an ovarian cyst is confirmed by a sonogram and not by an operative laparoscopy.

The positional sensor enabled Foley catheter would also help in any surgery that the position of the bladder needs to be adjusted to correct any urinary problem, such as when a woman cannot empty her bladder due to avulsion of the bladder through the vagina.

Another use for a positional sensor enabled Foley catheter would be to correct fecal incontinence, which is often another sequela of pregnancy and childbirth. An elongated rather than round apparatus would be inserted into the rectum and a different, but similar apparatus would be inserted into the vagina and the Foley catheter would be inserted into the bladder and all related to the pubic bone for correct positioning. With this information the surgeon would be able to properly position the anatomy surgically, in real time, therefore correcting the fecal incontinence.

A correct diagnosis of a surgically treatable case of urinary incontinence would be obtained by using the positional sensor enabled Foley catheter. In a vaginal approach surgery, the surgeon would insert the positional sensor enabled Foley catheter in the bladder and allow it to drain. The anterior vaginal wall would be peeled off exposing the urethra and the bladder neck. Sutures or a sling would be placed and held until ready. The Foley balloon would be inflated and its position inside the bladder would be measured relative to the pubic bone, coccyx or vagina. The surgeon would then tighten the sutures, visualizing the elevation of the bladder and the bladder neck on the computer screen until the correct angle is reached. This angle in the past has only been guessed at by the experience of the surgeon, giving rise to the high failure rate of this procedure.

Figure 1B:
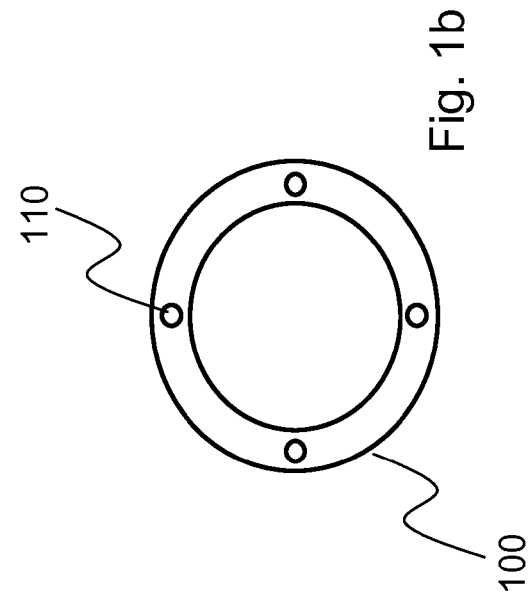

The positional feedback catheter of the present invention may incorporate, as depicted in FIG. 1b, positional sensors of varying types. For example, electromagnetic position determining systems provide a convenient method of receiving accurate information on the position and orientation of intrabody objects, and allow accurate tracking of these objects. Such systems are described for example in U.S. Pat. No. 5,558,091, U.S. Pat. No. 5,391,199 and U.S. Pat. No. 5,443,489, and in International Patent Publications WO94/04938 and WO96/05768. These systems determine the coordinates of a device using one or more field sensors, such as a Hall effect device, coils or other antennas carried on the device. The field sensors are transducers used as position sensors and are typically located at or adjacent the distal end of the device, and/or along the length of the device. Therefore, the transducers are preferably made as small as possible so as to fit into the device without interfering with the device's maneuverability or increasing its size unduly.

Most magnetic position determining systems use sensors formed of miniature coils that include a large number of turns of an electrically conducting wire. Such coils are described, for example, in PCT publications WO94/04938 and WO96/05768, in the above mentioned U.S. Pat. No. 5,391,199, and in PCT publication WO97/24983. To determine both translational and rotational coordinates, some position determining systems, such as the system described in PCT publication WO96/05768, use three sensor coils, having respective axes that are mutually linearly independent, preferably mutually orthogonal. Preferably, these three coils are packaged together to form a sensor assembly, which is used to provide six-dimensional position and orientation coordinate readings. The use of an assembly which has the three coils within one package allows easy insertion and/or attachment of the coils to devices such as catheters. Also, the assembly provides exact positioning of the coils relative to each other, thus simplifying the calibration of position determining systems using the coils. Generally, the coils are enclosed in a cylindrical-shaped case, which protects the coils from the surroundings.

U.S. Pat. No. 6,203,493 describes a method of enhancing the accuracy of position determination of an endoscope that includes miniature position sensing coils, by distancing the coils from metallic apparatus within the endoscope. If the coil assembly can be made with a smaller width, it is then possible to increase the separation between the miniature coils and the metallic apparatus, and thus achieve better accuracy from the position determining system. Coils made by photolithography or VLSI (very large scale integration) procedures have been disclosed in U.S. Pat. No. 6,201,387 B1, for example, where the photolithographic coils are generally made in the form of a spiral conductor printed on a substrate of plastic, ceramic or semiconductor material. Such coils conventionally comprise up to four overlapping spiral layers, using currently available fabrication techniques.

Reducing the width or outer diameter of the coil assembly would allow position determining systems to be used with narrower devices, which generally have superior maneuverability and ease of access to remote locations. Alternatively, reducing the width or outer diameter of the coil assembly would allow the assembly to occupy a smaller portion of the cross-sectional area of the device, leaving more space for functional apparatus and/or working channels along the devices. A positional sensor for a medical device comprising a core made of a Wiegand effect material and a winding circumferentially positioned around the core, has been disclosed in U.S. Pat. No. 7,286,868, and may be used to determine position and/or orientation coordinates.

The positional feedback catheter of the present invention may include a magnetic position sensor, which may comprise a number of coils for detecting signals emitted from a transmitter of a position tracking system. For example, the magnetic position sensor may comprise three mutually orthogonal coils. The transmitter may also include, for example, three mutually orthogonal emitting coils. The sensor may detect magnetic fields produced by the transmitter and the output of the sensor may be input to a position tracking processing unit of the position tracking system. Based on the signals received by the sensor, the position tracking processing unit may compute the position and orientation (roll, pitch, and yaw) of the sensor (and hence the position and orientation of the distal end of the catheter). The processing unit may comprise, for example, a printed circuit board with a processor and firmware for computing the position of the position based on the received signals. The processing unit may also input control signals to a drive control unit for the transmitter to activate selectively the desired output from the transmitter. A suitable position tracking system is described in U.S. patent application Publication No. 2004/0088136 A1, which is incorporated herein by reference.

Figure 2:
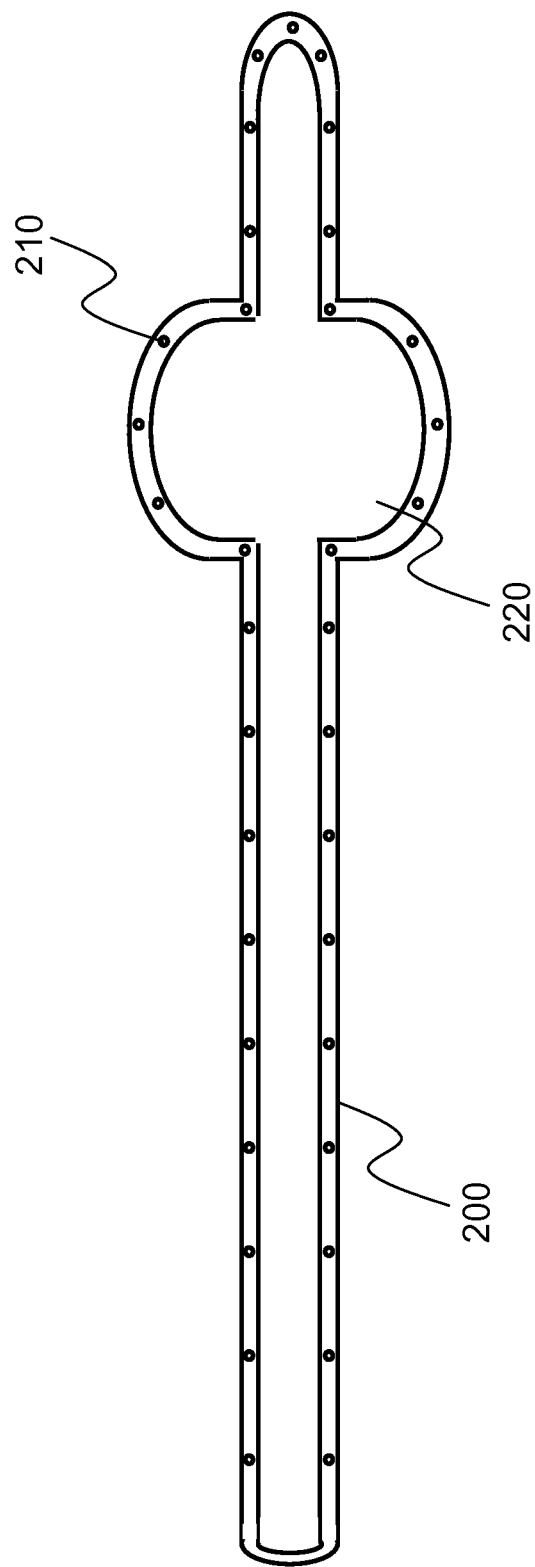
FIG. 2 is a cross-section of a further embodiment of the present invention.

FIG. 1a depicts a Foley catheter 100 with a firm tip, which may be about ½" inch in length to guide the Foley catheter through the urethra. There is a small hole in this portion to facilitate drainage of any urine in the bladder of the patient. Below the tip is a section that comprises an inflatable balloon, which, may be at least 10 cc in volume (e.g., about 100 cc). The cross section A of the device depicted in FIG. 1a is shown as FIG. 1b where the Foley catheter 100 has one or more positional sensors 110. In addition, FIG. 2 depicts a Foley catheter 200 has one or more positional sensors 210, where the inflatable balloon is expanded, and the compartment 220 filled with a solution such as saline. The number and precise placement of positional sensors (110 or 210) may vary depending on the type of positional sensor and positional tracking system employed.

SPECIFIC EXAMPLES

As described earlier, the present invention may embody positional sensors of varying types. These include, but are not limited to, sensors capable of providing positional feedback based on magnetic, electromagnetic, microelectromechanical, radio frequency, ultrasound and video, data. One example of a positional sensor enabled Foley catheter is a Foley catheter containing three microelectromechanical or MEMS devices: one 3-axis accelerometer, one roll/pitch gyroscope and one yaw rate gyroscope. The devices may be mounted on a small flexible printed circuit board (PCB) and then attached to the Foley. The 3-axis accelerometer tracks translation of the Foley catheter in three directions. The gyroscopes are utilized to account for gravitational rotation, allowing real time movement to be tracked.

A PCB is prepared with the three MEMS devices mounted thereon. Soft leads trail the MEMS devices to supporting devices, including, for example, a data acquisition card which may be used for transforming analog signals to digital signals. The PCB is set within the wall of the Foley catheter. Location of the Foley catheter may be determined by the output signals of the MEMS devices.

Detailed embodiments of the present invention are disclosed herein; however, it is to be understood that the disclosed embodiments are merely exemplary of the invention that may be embodied in various forms. It will be appreciated that many modifications and other variations that will be appreciated by those skilled in the art are within the intended scope of this invention as claimed below without departing from the teachings, spirit and intended scope of the invention.

What is claimed is:

1. A method for sensing the relative position of a patient bladder comprising inserting a positional sensor enabled catheter within the bladder, and determining the position of the bladder relative to at least one fixed reference point within the patient.

2. The method of claim 1, wherein said fixed reference point is the pubic bone, the coccyx, or the vagina.

3. The method of claim 1, wherein said method is performed on a patient in a real-time operation.

4. The method of claim 1, wherein said method is performed on a patient at multiple time intervals surrounding an event.

5. The method of claim 4, wherein said intervals surrounding an event includes at least one pre-event and at least one post-event measurement.

6. The method of claim 5, wherein said event is pregnancy or menopause.

7. A method for treating female stress incontinence comprising inserting a positional sensor enabled catheter within a patient bladder, determining the position of the bladder relative to a fixed reference point within the patient; and manipulating the bladder to a position suitable for alleviating the incontinence.

8. The method of claim 7, wherein said fixed reference point is the pubic bone, the coccyx or the vagina.

9. The method of claim 7, wherein said method is performed on a patient in a real-time operation.

10. The method of claim 7, wherein said method is performed on a patient at multiple time intervals surrounding an event.

11. The method of claim 10, wherein said intervals surrounding an event includes at least one pre-event and at least one post-event measurement.

12. The method of claim 11, wherein said event is pregnancy or menopause.

* * * * *